(12) United States Patent
Whitman et al.

(10) Patent No.: US 7,138,535 B1
(45) Date of Patent: Nov. 21, 2006

(54) DIRECT EPOXIDATION PROCESS

(75) Inventors: Peter J. Whitman, Glen Mills, PA (US); Jay F. Miller, Chester Springs, PA (US); John H. Speidel, Jr., Media, PA (US); Robert N. Cochran, West Chester, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 43 days.

(21) Appl. No.: 11/141,962

(22) Filed: Jun. 1, 2005

(51) Int. Cl.
*C07D 301/06* (2006.01)
*C07D 301/12* (2006.01)

(52) U.S. Cl. ..................... 549/533; 549/531
(58) Field of Classification Search ............... 549/531, 549/533
See application file for complete search history.

(56) References Cited

U.S. PATENT DOCUMENTS

| | | | |
|---|---|---|---|
| 3,351,635 A | 11/1967 | Kollar | 260/348.5 |
| 4,367,342 A | 1/1983 | Wulff et al. | 549/529 |
| 4,833,260 A | 5/1989 | Neri et al. | 549/531 |
| 5,859,265 A | 1/1999 | Müller et al. | 549/531 |
| 6,005,123 A | 12/1999 | Dessau et al. | 549/531 |
| 6,008,388 A | 12/1999 | Dessau et al. | 549/531 |
| 6,399,794 B1 | 6/2002 | Hancu | 549/533 |
| 6,555,493 B1 | 4/2003 | Cooker et al. | 502/74 |

FOREIGN PATENT DOCUMENTS

| | | |
|---|---|---|
| BE | 1001038 A7 | 6/1989 |
| JP | 4-352771 | 12/1992 |
| WO | WO 98/00413 | 1/1998 |

OTHER PUBLICATIONS

Li et al, Reaction Kinetics and Catalysis Letters, vol. 82, No. 1, p. 73-80 (2004).*

\* cited by examiner

*Primary Examiner*—Bernard Dentz
(74) *Attorney, Agent, or Firm*—Kevin M. Carroll

(57) ABSTRACT

The invention is a process for epoxidizing an olefin with hydrogen and oxygen in the presence of a catalyst comprising a noble metal and a titanium or vanadium zeolite in a solvent mixture comprising water, methanol, and a $C_3$–$C_6$ aliphatic ketone. This process surprisingly gives significantly reduced by-product glycol and glycol ethers formed by the unwanted ring-opening of epoxides.

20 Claims, No Drawings

DIRECT EPOXIDATION PROCESS

FIELD OF THE INVENTION

This invention relates to an epoxidation process which comprises reacting olefin, hydrogen, and oxygen in the presence of a catalyst comprising a noble metal and a titanium or vanadium zeolite in a solvent mixture comprising water, methanol, and a $C_3$–$C_6$ aliphatic ketone. Surprisingly, the process results in decreased ring-opening of the epoxide product and thus lowers selectivity to by-product glycols and glycol ethers.

BACKGROUND OF THE INVENTION

Many different methods for the preparation of epoxides have been developed. Generally, epoxides are formed by the reaction of an olefin with an oxidizing agent in the presence of a catalyst. The production of propylene oxide from propylene and an organic hydroperoxide oxidizing agent, such as ethylbenzene hydroperoxide or tert-butyl hydroperoxide, is commercially practiced technology. This process is performed in the presence of a solubilized molybdenum catalyst, see U.S. Pat. No. 3,351,635, or a heterogeneous titania on silica catalyst, see U.S. Pat. No. 4,367,342. Another commercially practiced technology is the direct epoxidation of ethylene to ethylene oxide by reaction with oxygen over a silver catalyst. Unfortunately, the silver catalyst has not proved useful in commercial epoxidation of higher olefins.

Besides oxygen and alkyl hydroperoxides, another oxidizing agent useful for the preparation of epoxides is hydrogen peroxide. U.S. Pat. No. 4,833,260, for example, discloses the epoxidation of olefins with hydrogen peroxide in the presence of a titanium silicate catalyst.

Much current research is conducted in the direct epoxidation of olefins with oxygen and hydrogen. In this process, it is believed that oxygen and hydrogen react in situ to form an oxidizing agent. Many different catalysts have been proposed for use in the direct epoxidation of higher olefins. Typically, the catalyst comprises one or more noble metals supported on a titanosilicate. For example, JP 4-352771 discloses the formation of propylene oxide from propylene, oxygen, and hydrogen using a catalyst containing a Group VIII metal such as palladium on a crystalline titanosilicate. The Group VIII metal is believed to promote the reaction of oxygen and hydrogen to form an in situ oxidizing agent. U.S. Pat. No. 5,859,265 discloses a catalyst in which a platinum metal, selected from Ru, Rh, Pd, Os, Ir and Pt, is supported on a titanium or vanadium silicalite. Other direct epoxidation catalyst examples include gold supported on titanosilicates, see for example PCT Intl. Appl. WO 98/00413.

One disadvantage of the described direct epoxidation catalysts is that they are prone to produce by-products such as glycols or glycol ethers formed by the ring-opening of the epoxide product or alkane by-product formed by the hydrogenation of olefin. U.S. Pat. No. 6,008,388 describes a direct olefin epoxidation process in which the selectivity for the reaction of olefin, oxygen, and hydrogen in the presence of a noble metal-modified titanium zeolite is enhanced by the addition of a nitrogen compound such as ammonium hydroxide to the reaction mixture. U.S. Pat. No. 6,399,794 teaches the use of ammonium bicarbonate modifiers to decrease the production of ring-opened by-products. U.S. Pat. No. 6,005,123 teaches the use of phosphorus, sulfur, selenium or arsenic modifiers such as benzothiophene to decrease the production of propane.

As with any chemical process, it is desirable to attain still further improvements in the epoxidation methods and catalysts. We have discovered an effective, convenient process to form an epoxidation catalyst and its use in the epoxidation of olefins.

SUMMARY OF THE INVENTION

The invention is an olefin epoxidation process that comprises reacting olefin, hydrogen, and oxygen in the presence of a catalyst comprising a noble metal and a titanium or vanadium zeolite in a solvent comprising water, methanol, and a $C_3$–$C_6$ aliphatic ketone. This process surprisingly gives significantly reduced by-product glycol and glycol ethers formed by the unwanted ring-opening of the product epoxide.

DETAILED DESCRIPTION OF THE INVENTION

The process of the invention employs a catalyst that comprises a noble metal and a titanium or vanadium zeolite. Titanium or vanadium zeolites comprise the class of zeolitic substances wherein titanium or vanadium atoms are substituted for a portion of the silicon atoms in the lattice framework of a molecular sieve. Such substances are well known in the art. Particularly preferred titanium zeolites include the class of molecular sieves commonly referred to as titanium silicalites, particularly "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Titanium-containing molecular sieves having framework structures isomorphous to zeolite beta, mordenite, ZSM-48, ZSM-12, MCM-22(MWW), and MCM-41 are also suitable for use. The titanium zeolites preferably contain no elements other than titanium, silicon, and oxygen in the lattice framework, although minor amounts of boron, iron, aluminum, sodium, potassium, copper and the like may be present.

The catalyst employed in the process of the invention also contains a noble metal. While any of the noble metals can be utilized (i.e., gold, silver, platinum, palladium, iridium, ruthenium, osmium), either alone or in combination, palladium or a palladium/gold combination is particularly desirable. Typically, the amount of noble metal present in the catalyst will be in the range of from 0.001 to 20 weight percent, preferably 0.005 to 10 weight percent, and particularly 0.01 to 5 weight percent.

The manner in which the noble metal is incorporated into the catalyst is not considered to be particularly critical. For example, the noble metal may be supported on the titanium or vanadium zeolite by impregnation, adsorption, ion-exchange, precipitation. Alternatively, the noble metal may be first supported on another support such as an inorganic oxide, inorganic chloride, carbon, or organic polymer resins, or the like, and then physically mixed with the titanium zeolite. Preferred inorganic oxides include oxides of Group 2, 3, 4, 5, 6, 13, or 14 elements. Particularly preferred inorganic oxide supports include silica, alumina, titania, zirconia, niobium oxides, tantalum oxides, molybdenum oxides, tungsten oxides, amorphous titania-silica, amorphous zirconia-silica, amorphous niobia-silica, and the like. Preferred organic polymer resins include polystyrene, styrene-divinylbenzene copolymers, crosslinked polyethyleneimines, and polybenzimidizole. Suitable supports also include organic polymer resins grafted onto inorganic oxide supports, such as polyethylenimine-silica. Preferred supports also include carbon. Particularly preferred supports include carbon, titania, zirconia, niobium oxides, silica, alumina, silica-alumina, tantalum oxides, molybdenum oxides, tungsten oxides, titania-silica, zirconia-silica, niobia-silica, and mixtures thereof.

There are no particular restrictions regarding the choice of noble metal compound used as the source of the noble metal. For example, suitable compounds include the nitrates, sulfates, halides (e.g., chlorides, bromides), carboxylates (e.g. acetate), and amine complexes of noble metals.

Particularly preferred catalysts useful in the process of the invention are noble metal-containing titanium or vanadium zeolite catalysts. Noble metal-containing titanium or vanadium zeolite catalysts are well known in the art and are described, for example, in JP 4-352771 and U.S. Pat. Nos. 5,859,265 and 6,555,493, the teachings of which are incorporated herein by reference in their entirety. Such catalysts typically comprise a noble metal (such as palladium, gold, platinum, silver, iridium, ruthenium, osmium, or combinations thereof supported on a titanium or vanadium zeolite. The noble metal-containing titanium or vanadium zeolite catalysts may contain a mixture of noble metals. Preferred noble metal-containing titanium or vanadium zeolite catalysts comprise palladium and a titanium or vanadium zeolite; palladium, gold, and a titanium or vanadium zeolite; or palladium, platinum, and titanium or vanadium zeolite.

The typical amount of noble metal present in the noble metal-containing titanium or vanadium zeolite will be in the range of from about 0.001 to 20 weight percent, preferably 0.005 to 10 weight percent, and particularly 0.01 to 5 weight percent. The manner in which the noble metal is incorporated into the noble metal-containing titanium or vanadium zeolite catalyst is not considered to be particularly critical. For example, the noble metal may be supported on the zeolite by impregnation or the like. Alternatively, the noble metal can be incorporated into the zeolite by ion-exchange with, for example, tetraammine palladium dichloride.

The noble metal-containing titanium or vanadium zeolite catalyst may also comprise a mixture of palladium-containing titanium or vanadium zeolite and palladium-free titanium or vanadium zeolite. The palladium-free titanium or vanadium zeolite is a titanium or vanadium-containing molecular sieve that is free of added palladium. The addition of a palladium-free titanium or vanadium zeolite has proven beneficial to productivity of the palladium that is present in the catalyst.

The noble metal-containing titanium or vanadium zeolite catalyst may be used in the epoxidation process as a powder or as a large particle size solid. Preferably, the noble metal-containing titanium or vanadium zeolite is spray dried, pelletized or extruded prior to use in epoxidation. If spray dried, pelletized or extruded, the catalyst may additionally comprise a binder or the like and may be molded, spray dried, shaped or extruded into any desired form prior to use in epoxidation. The noble metal-containing titanium or vanadium zeolite may also be encapsulated in polymer as described in copending U.S. application Ser. No. 10/796,680, the teachings of which are incorporated herein by reference in their entirety.

The epoxidation process of the invention comprises contacting an olefin, oxygen, and hydrogen in the presence of the catalyst in a solvent mixture. Suitable olefins include any olefin having at least one carbon—carbon double bond, and generally from 2 to 60 carbon atoms. Preferably the olefin is an acyclic alkene of from 2 to 30 carbon atoms; the process of the invention is particularly suitable for epoxidizing $C_2$–$C_6$ olefins. More than one double bond may be present, as in a diene or triene for example. The olefin may be a hydrocarbon (i.e., contain only carbon and hydrogen atoms) or may contain functional groups such as halide, carboxyl, hydroxyl, ether, carbonyl, cyano, or nitro groups, or the like. The process of the invention is especially useful for converting propylene to propylene oxide.

Oxygen and hydrogen are also required for the epoxidation process. Although any sources of oxygen and hydrogen are suitable, molecular oxygen and molecular hydrogen are preferred.

Epoxidation according to the invention is carried out at a temperature effective to achieve the desired olefin epoxidation, preferably at temperatures in the range of 0–250° C., more preferably, 20–100° C. The molar ratio of hydrogen to oxygen can usually be varied in the range of $H_2:O_2=1:10$ to 5:1 and is especially favorable at 1:5 to 2:1. The molar ratio of oxygen to olefin is usually 2:1 to 1:20, and preferably 1:1 to 1:10. A carrier gas may also be used in the epoxidation process. As the carrier gas, any desired inert gas can be used. The molar ratio of olefin to carrier gas is then usually in the range of 100:1 to 1:10 and especially 20:1 to 1:10.

As the inert gas carrier, noble gases such as helium, neon, and argon are suitable in addition to nitrogen and carbon dioxide. Saturated hydrocarbons with 1–8, especially 1–6, and preferably with 1–4 carbon atoms, e.g., methane, ethane, propane, and n-butane, are also suitable. Nitrogen and saturated $C_1$–$C_4$ hydrocarbons are the preferred inert carrier gases. Mixtures of the listed inert carrier gases can also be used.

Specifically in the epoxidation of propylene, propane can be supplied in such a way that, in the presence of an appropriate excess of carrier gas, the explosive limits of mixtures of propylene, propane, hydrogen, and oxygen are safely avoided and thus no explosive mixture can form in the reactor or in the feed and discharge lines.

The amount of catalyst used may be determined on the basis of the molar ratio of the titanium contained in the titanium zeolite to the olefin that is supplied per unit time. Typically, sufficient catalyst is present to provide a titanium/olefin per hour molar feed ratio of from 0.0001 to 0.1.

The process of the invention is carried out in the liquid phase in the presence of a solvent mixture comprising methanol, water, and a $C_3$–$C_6$ aliphatic ketone. The solvent mixture is preferably a single liquied phase. Preferred $C_3$–$C_6$ aliphatic ketones include acetone and methyl ethyl ketone. The specific amount of methanol, water and ketone that comprise the solvent mixture is not a critical feature of the invention. However, preferably the solvent mixture comprises 5–80 volume percent methanol, 5–50 volume percent water, and 5–80 volume percent ketone. It is most preferable if the solvent mixture comprises 10–70 volume percent methanol, 10–40 volume percent water, and 10–70 volume percent ketone. In the liquid phase process of the invention, the catalyst is preferably in the form of a suspension or fixed-bed. The process may be performed using a continuous flow, semi-batch or batch mode of operation. It is advantageous to work at a pressure of 1–100 bars.

In addition to the solvent mixture, it may be advantageous to use a buffer. The buffer may typically be added to the solvent mixture to form a buffer solution, or the solvent mixture and buffer may be added separately. The buffer solution is employed in the reaction to inhibit the formation of glycols or glycol ethers during epoxidation. Buffers are well known in the art.

Buffers useful in this invention include any suitable salts of oxyacids, the nature and proportions of which in the mixture, are such that the pH of their solutions may preferably range from 3 to 12, more preferably from 4 to 10 and most preferably from 5 to 9. Suitable salts of oxyacids contain an anion and cation. The anion portion of the salt may include anions such as phosphate, carbonate, bicarbonate, carboxylates (e.g., acetate, phthalate, and the like), citrate, borate, hydroxide, silicate, aluminosilicate, or the like. The cation portion of the salt may include cations such as ammonium, alkylammoniums (e.g., tetraalkylammoniums, pyridiniums, and the like), alkali metals, alkaline earth metals, or the like. Cation examples include $NH_4$, $NBu_4$, $NMe_4$, Li, Na, K, Cs, Mg, and Ca cations. Buffers may preferably contain a combination of more than one suitable salt. Typically, the concentration of buffer in the solvent is from about 0.0001 M to about 1 M, preferably from about 0.0005 M to about 0.3 M. The buffer useful in this invention may also include the addition of ammonia gas or ammonium hydroxide to the reaction system. For instance, one may use a pH=12–14 solution of ammonium hydroxide to balance the pH of the reaction system. More preferred buffers include alkali metal phosphate, ammonium phosphate, and ammonium hydroxide buffers.

The following examples merely illustrate the invention. Those skilled in the art will recognize many variations that are within the spirit of the invention and scope of the claims.

EXAMPLE 1

Catalyst Preparation

Catalyst 1A: 100 parts by weight of a spray dried TS-1 (80% TS-1, silica binder, 2.1 wt. % Ti, calcined at 550° C. in air) is slurried in deionized water (250 parts by weight) in a mix tank and agitated at 500 rpm. The pH is adjusted to 7.0 with 3 wt. % ammonium hydroxide and an aqueous solution of tetraamine palladium dinitrate (containing 0.105 parts by weight palladium) is then added while maintaining pH at 7.0 by adding 3 wt. % ammonium hydroxide. The pH is then adjusted to 7.5 with 3 wt. % ammonium hydroxide solution and the slurry is stirred at 30° C. for an additional 60 minutes. The slurry is allowed to settle and the solid is decanted and water washed (110 parts by weight water, three times), then the solid cake is filtered. The solids are vacuum dried at 50° C. for 6 hours, calcined in air at 300° C. for 4 hours, then treated at 100° C. with 4 vol. % hydrogen in nitrogen for 1 hour. Catalyst 1 A contains 0.1 wt. % Pd and 2.1 wt. % Ti.

Catalyst 1B: Catalyst 1B is made according to the procedure of Catalyst 1A, with the exception that the spray dried TS-1 contained 60% TS-1 and a 40% mixture of kaolin and alumina binder. The final catalyst product was calcined in air at 350° C. for 4 hours and reduced in hydrogen at 50° C. for 4 hours.

EXAMPLE 2

Propylene Epoxidation Studies

Runs 2A–2G: To evaluate the use of methanol, acetone, and water mixtures in olefin epoxidation using Catalyst 1A, the epoxidation of propylene using oxygen and hydrogen is carried out. The following procedure is employed.

The reaction system consists of a 1000-cc stainless steel CSTR type reactor. Gas and liquid feeds enter the reactor, and the vapor exits the reactor through a port at the top of the reactor, while the liquid exits through a filter which keeps the catalyst in the reactor. The reaction solvent consists of a mixture of methanol, acetone, and water in the feed amounts shown in Table 1. Ammonium phosphate solution (pH=7.2, 0.1 M) is added to the reactor through a separate feed line resulting in a final buffer concentration 2 mM. Catalyst 1A (18 g) and the reaction solvent (600 mL) are added to the reactor as a slurry. The slurry in the reactor is heated to 60° C. under about 500 psig, and is stirred at 500 rpm. Additional reaction solvent is pumped through the reactor at a rate of about 100 g/hr. The gas flow rates were about 300 SLPH (standard liters per hour) of nitrogen, 300 SLPH of 8 vol. % oxygen in nitrogen, 12 SLPH hydrogen, and 75 g/hr propylene. Propylene oxide and equivalents ("POE") are produced during the reaction. POE produced include propylene oxide ("PO") and the ring-opened products ("RO") propylene glycol and glycol ethers. The products coming out of the reactor (in both vapor and liquid phase) are analyzed by GC. The results of the GC analyses are used to calculate the selectivities shown in Table 1.

Runs 2H–2L: To evaluate the use of methyl ethyl ketone (in place of acetone), methanol, and water mixtures in olefin epoxidation using Catalyst 1A, the epoxidation of propylene using oxygen and hydrogen is carried out according to the procedure of Runs 2A–2G.

Runs 2M–2P: To evaluate the use of acetone or methyl ethyl ketone (mixed with methanol and water) in olefin epoxidation using Catalyst 1B, the epoxidation of propylene using oxygen and hydrogen is carried out according to the procedure of Runs 2A–2G.

The results indicate that a significant decrease in ring-opening is seen where a mixture of ketone, methanol, and water is used as the reaction solvent compared to a methanol:water or ketone:water solvent mixture. The results also indicate that although methyl ethyl ketone is not as active as acetone in mixtures with methanol and water, non-selective ring-opening is negligible using methyl ethyl ketone.

TABLE 1

EPOXIDATION USING ACETONE OR MEK WITH METHANOL, AND WATER

| Run # | Feed Amounts (Wt. %) | | | | PO Rate[1] | POE Rate[2] | Ring Opening Rate[3] | By-product Amounts (Wt. %) | |
|---|---|---|---|---|---|---|---|---|---|
| | MeOH | Acetone | MEK | $H_2O$ | | | | PG | PM1 + PM2 |
| 2A* | 75 | 0 | — | 25 | 0.26 | 0.31 | 0.033 | 0.23 | 0.8 |
| 2B | 50 | 25 | — | 25 | 0.28 | 0.3 | 0.024 | 0.22 | 0.49 |
| 2C* | 0 | 75 | — | 25 | 0.12 | 0.14 | 0.045 | 0.46 | 0 |
| 2D* | 75 | 0 | — | 25 | 0.25 | 0.32 | 0.045 | 0.32 | 1.21 |
| 2E | 10 | 65 | — | 25 | 0.19 | 0.22 | 0.022 | 0.33 | 0.15 |

TABLE 1-continued

EPOXIDATION USING ACETONE OR MEK WITH METHANOL, AND WATER

| Run # | Feed Amounts (Wt. %) | | | | PO Rate[1] | POE Rate[2] | Ring Opening Rate[3] | By-product Amounts (Wt. %) | |
|---|---|---|---|---|---|---|---|---|---|
| | MeOH | Acetone | MEK | H$_2$O | | | | PG | PM1 + PM2 |
| 2F | 37.5 | 37.5 | — | 25 | 0.23 | 0.27 | 0.020 | 0.26 | 0.41 |
| 2G* | 75 | 0 | — | 25 | 0.26 | 0.32 | 0.045 | 0.35 | 1.01 |
| 2H* | 75 | — | 0 | 25 | 0.3 | 0.37 | 0.05 | 0.25 | 1.2 |
| 2I | 50 | — | 10 | 25 | 0.25 | 0.28 | 0.03 | 0.15 | 0.56 |
| 2J | 50 | — | 25 | 25 | 0.17 | 0.19 | 0.02 | 0.09 | 0.20 |
| 2K | 50 | — | 50 | 25 | 0.09 | 0.095 | 0.005 | 0.0004 | 0.0005 |
| 2L | 67 | — | 8 | 25 | 0.03 | 0.03 | 0.01 | 0.03 | 0 |
| 2M* | 75 | 0 | 0 | 25 | 0.15 | 0.22 | 0.07 | 0.25 | 1.38 |
| 2N | 50 | 25 | 0 | 25 | 0.13 | 0.14 | 0.01 | 0 | 0.17 |
| 2O[4] | 50 | 25 | 0 | 25 | 0.18 | 0.21 | 0.03 | 0.2 | 0.57 |
| 2P | 50 | 0 | 25 | 25 | 0.11 | 0.11 | 0.003 | 0.05 | 0 |

*Comparative Example
[1]PO Rate = grams PO produced/gram of catalyst per hour.
[2]POE Rate = grams POE produced/gram of catalyst per hour.
[3]Ring Opening Rate = grams RO produced/gram of catalyst per hour per percent PO in the liquid.
[4]This run was performed at 70° C.

We claim:

1. A process for producing an epoxide comprising reacting an olefin, oxygen, and hydrogen in the presence of a catalyst in a solvent mixture comprising water, methanol, and one or more C$_3$–C$_6$ aliphatic ketones, wherein the catalyst comprises a noble metal and a titanium or vanadium zeolite.

2. The process of claim 1 wherein the catalyst is a noble metal-containing titanium or vanadium zeolite.

3. The process of claim 2 wherein the catalyst comprises a titanium silicalite and palladium.

4. The process of claim 2 wherein the catalyst comprises a titanium silicalite, palladium, and one or more metals selected from the group consisting of gold and platinum.

5. The process of claim 2 wherein the catalyst comprises a palladium-containing titanium or vanadium zeolite and a palladium-free titanium or vanadium zeolite.

6. The process of claim 1 wherein the noble metal is combined with a support.

7. The process of claim 6 wherein the noble metal is selected from the group consisting of palladium and gold.

8. The process of claim 6 wherein the support is selected from the group consisting of carbon, titania, zirconia, niobium oxides, silica, alumina, silica-alumina, tantalum oxides, molybdenum oxides, tungsten oxides, titania-silica, zirconia-silica, niobia-silica, and mixtures thereof.

9. The process of claim 1 wherein the olefin is a C$_2$–C$_6$ olefin.

10. The process of claim 1 wherein the olefin is propylene.

11. The process of claim 1 wherein the solvent mixture comprises 5–80 volume percent methanol, 5–50 volume percent water, and 5–80 volume percent ketone.

12. The process of claim 1 wherein the ketone is acetone.

13. The process of claim 1 wherein the ketone is methyl ethyl ketone.

14. A process for producing propylene oxide comprising reacting propylene, hydrogen and oxygen in the presence of a palladium-containing titanium zeolite catalyst in a solvent mixture comprising water, methanol, and a C$_3$–C$_6$ aliphatic ketone.

15. The process of claim 14 wherein the catalyst comprises a titanium silicalite and palladium.

16. The process of claim 14 wherein the catalyst comprises a titanium silicalite, palladium, and one or more metals selected from the group consisting of gold and platinum.

17. The process of claim 14 wherein the catalyst comprises a palladium-containing titanium zeolite and a palladium-free titanium zeolite.

18. The process of claim 14 wherein the solvent mixture comprises 5–80 volume percent methanol, 5–50 volume percent water, and 5–80 volume percent ketone.

19. The process of claim 14 wherein the ketone is acetone.

20. The process of claim 14 wherein the ketone is methyl ethyl ketone.

* * * * *